United States Patent [19]

Nagase et al.

[11] 4,246,424
[45] Jan. 20, 1981

[54] METHOD FOR RACEMIZATION OF OPTICALLY ACTIVE AMINES

[75] Inventors: Tsuneyuki Nagase, Takatsuki; Gohu Suzukamo, Ibaraki; Yoshio Suzuki, Itami, all of Japan

[73] Assignee: Sumitomo Chemical Company, Limited, Osaka, Japan

[21] Appl. No.: 686,575

[22] Filed: May 14, 1976

Related U.S. Application Data

[62] Division of Ser. No. 500,927, Aug. 27, 1974, abandoned.

[30] Foreign Application Priority Data

Aug. 31, 1973 [JP] Japan .................................. 48/98575
Sep. 1, 1973 [JP] Japan .................................. 48/98558

[51] Int. Cl.³ ..................... C07C 87/28; C07C 101/02; C07C 101/32
[52] U.S. Cl. ........................................ 560/38; 560/40; 560/155; 560/171; 564/321; 564/371; 564/391; 564/392; 564/387
[58] Field of Search ........ 260/471 A, 482 R, 570.5 R, 260/570.8 R, 570.0 R, 471 R, 422 R

[56] References Cited

U.S. PATENT DOCUMENTS

| | | | |
|---|---|---|---|
| 2,214,034 | 9/1940 | Tabern | 260/570.6 X |
| 3,168,566 | 2/1965 | Lotes et al. | 260/570.8 |
| 3,193,590 | 7/1965 | Hsieh | 260/665 |
| 3,970,700 | 7/1976 | Nagase et al. | 260/570.8 |

OTHER PUBLICATIONS

Suga et al., "Chemistry & Industry", (1969), No. 3, p. 78.

Primary Examiner—Robert V. Hines
Attorney, Agent, or Firm—Birch, Stewart, Kolasch & Birch

[57] ABSTRACT

A method for racemization of optically active amines which comprises contacting an optically active amine of the formula:

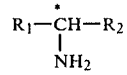

wherein C* is an asymmetric carbon atom, $R_1$ is alkyl, aralkyl or aryl and $R_2$ is aryl or alkoxycarbonyl, the aryl or aralkyl moiety bearing optionally one or more alkyl or alkoxy groups on the aromatic ring, provided that $R_1$ and $R_2$ are always different from each other, with a catalyst comprising an alkali metal and a polycyclic aromatic hydrocarbon until a sufficient amount of the optically active amine is racemized.

7 Claims, No Drawings

METHOD FOR RACEMIZATION OF OPTICALLY ACTIVE AMINES

This application is a division of copending application Ser. No. 500,927, filed on Aug. 27, 1974 and now abandoned.

The present invention relates to a method for racemization of optically active amines.

The optically active amines which can be racemized by the present invention are representable by the formula:

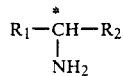
[I]

wherein C* is an asymmetric carbon atom, $R_1$ is alkyl, aralkyl or aryl and $R_2$ is aryl or alkoxycarbonyl, the aryl or aralkyl moiety bearing optionally one or more alkyl or alkoxy groups on the aromatic ring, provided that $R_1$ and $R_2$ are always different from each other.

Optically active amines [I] are useful as industrial chemicals, agricultural chemicals, and the like. They are also useful as intermediates in the production of useful chemical substances. In general, these optically active amines [I] are industrially produced in the form of racemic mixtures, which are then subjected to resolution. After separation of the optical antipodes which are useful, the remaining undesirable antipodes are subjected to racemization and resolution, whereby the optical antipodes which are useful are additionally obtained. Thus, racemization is one of the valuable methods for production of the optical active amines [I].

As the result of the extensive study on an racemization of optically active amines [I], it has now been surprisingly found that a catalyst comprising an alkali metal and a polycyclic aromatic hydrocarbon is quite effective in the racemization of said amines and can afford their racemic mixtures in quantitative yields.

According to the present invention, the optically active amine [I] is contacted with a catalyst comprising an alkali metal and a polycyclic aromatic hydrocarbon until a sufficient amount is racemized.

The optically active amine to which this invention is applicable is the one represented by the formula [I] wherein $R_1$ is preferably alkyl having not more than 8 carbon atoms (e.g. methyl, ethyl, propyl, isopropyl, butyl, sec.-butyl, t-butyl, cyclohexyl, cyclohexylmethyl), aralkyl having not more than 18 carbon atoms (e.g. benzyl, phenethyl, naphthylmethyl, naphthylethyl) or aryl having not more than 18 carbon atoms (e.g. phenyl, naphthyl) and $R_2$ is favorably aryl having not more than 18 carbon atoms (e.g. phenyl, naphthyl) or alkoxycarbonyl having not more than 9 carbon atoms (e.g. methoxycarbonyl, ethoxycarbonyl, propoxycarbonyl, isopropoxycarbonyl, butoxycarbonyl, sec.-butoxycarbonyl, t-butoxycarbonyl, cyclohexyloxycarbonyl). Among the said significances of the symbols $R_1$ and $R_2$, the aryl or aralkyl moiety may bear one or more alkyl or alkoxy groups of not more than 4 carbon atoms on the aromatic ring. Specific examples of the optically active amine [I] are α,β-diphenylethylamine, α-phenyl-β-(o-tolyl)-ethylamine, α-phenyl-β-(m-tolyl)ethylamine, α-phenyl-β-(p-tolyl)ethylamine, β-phenyl-α-(o-tolyl)ethylamine, β-phenyl-α-(m-tolyl)ethylamine, β-phenyl-α-(p-tolyl)ethylamine, α-methylbenzylamine, α-ethylbenzylamine, α-(1-naphthyl)ethylamine, α-(2-naphthyl)-ethylamine, alanine methyl ester, alanine butyl ester, norvaline propyl ester, leucine ethyl ester, β-cyclohexylalanine methyl ester, β-phenylalanine methyl ester, β-phenylalanine propyl ester, β-3,4-dimethoxyphenylalanine ethyl ester, etc.

The optically active amine [I] may include the d-form and/or l-form in any proportion.

The catalyst used in the method of this invention comprises as the essential components an alkali metal (e.g. lithium, sodium, potassium) and a polycyclic aromatic hydrocarbon (e.g. naphthalene, alkylnaphthalene, anthracene, phenanthrene, tetraphenylethylene). Thus, such catalyst composition may be, for instance, lithium naphthalene, sodium naphthalene, potassium naphthalene, lithium anthracene, sodium anthracene, potassium anthracene, etc. Among these catalysts, sodium naphthalene and potassium naphthalene are preferred from the industrial point of view. The alkali metal and the polycyclic aromatic hydrocarbon are known to form a soluble, colored complex in the presence of an ether (e.g. dimethyl ether, diethyl ether, ethylene glycol dimethyl ether, tetrahydrofuran) [J. Am. Chem. Soc., 58, 2442 (1936)], and such complex is also utilizable as the catalyst in this invention.

The racemization may be performed batchwise or continuously. The optically active amine [I] may be introduced alone or together with the catalyst into a reactor wherein the racemization is effected. When desired, it may be introduced into the reactor successively or intermittently depending on the proceeding of the racemization.

The proportion of the catalyst to the optically active amine [I] does not have to be controlled strictly. Thus, the catalyst may be used in such an amount that an appropriate yield of the racemic mixture is obtained within a proper reaction time. From the economical point of view, however, the catalyst is usually employed in an amount of about 1/1000 to 1/5 mole, preferably of about 1/200 to 1/10 mole to 1 mole of the said amine [I].

The reaction temperature is usually from about $-10°$ to 150° C., favorably from about $-10°$ to 100° C. When the reaction temperature is lower than about $-10°$ C., the rate of racemization is too slow. When higher than about 150° C., the rate of racemization is faster but the decomposition of the optically active amine [I] and/or any other unfavorable side reaction may take place.

The racemization can proceed quantitatively even if any solvent is not present. If desired, there may be used any solvent which does not afford any unfavorable influence on the proceeding of the racemization. In order to accomplish the racemization assuredly, the operation may be carried out under the atmosphere of any inert gas. Further, the elimination of any water or moisture from the optically active amine [I] prior to the contact with the catalyst is ordinarily favored.

The reaction time is more or less associated with the amount of the catalyst and the reaction temperature. It is usually more shortened with a larger amount of the catalyst and a higher reaction temperature.

The proceeding of the racemization can be traced, for instance, by measuring the optical rotation at a certain concentration or by analyzing with gas-chromatography.

After completion of the reaction, the recovery of the product may be carried out by a conventional separation procedure. For instance, the reaction mixture is, after elimination of the catalyst therefrom, treated by distillation or chromatography. The purification may be also carried out with the formation of the salt of the resultant amine [I] with an acid. Since the racemization proceeds quantitatively, the reaction product may be of high purity, even if any purification procedure is not applied.

By the method of this invention, racemization can be carried out quantitatively using a small amount of the catalyst under a mild condition. Accordingly, it is quite convenient from the viewpoints of operation, apparatus and economy.

Practical and presently preferred embodiments of this invention are illustratively shown in the following Examples.

EXAMPLE 1

In a 100 ml reactor, there was charged (−)-α-phenyl-β-(p-tolyl)ethyl amine ($[\alpha]_D^{25}$ −12.5° (neat)) (50 g) under nitrogen. After sodium naphthalene (sodium:naphthalene=15.2:84.8 by weight, i.e. 1:1 by mole) (2.5 g) was added thereto, the resultant mixture was stirred at 25° C. The optical rotation of the reaction mixture measured with elapses of the reaction time was as shown in Table 1.

TABLE 1

| Reaction time (hrs.) | Optical rotation $[\alpha]_D^{25}$ (neat) |
| --- | --- |
| 0 | −12.5° |
| 0.5 | −9.3° |
| 1 | −4.2° |
| 2 | −1.8° |
| 3 | −0.8° |
| 4 | −0.3° |

After completion of the reaction, a small amount of methanol was added to the reaction mixture so as to inactivate the catalyst, hydrochloric acid was added thereto to make the amine hydrochloride and then neutral substances such as naphthalene were eliminated by extraction. The salt was decomposed by the addition of a 20% aqueous solution of sodium hydroxide, and the liberated amine was extracted with toluene. The toluene extract was concentrated and then distilled under reduced pressure to give racemic α-phenyl-β-(p-tolyl)ethylamine (42.5 g) as a fraction boiling at 120° to 123° C./0.2 mmHg. $n_D^{25}$ 1.5668.

EXAMPLE 2

As in Example 1, racemization was carried out. The optical rotation and the yield of the product with variation of the reaction temperature and the reaction time were as shown in Table 2.

TABLE 2

| Reaction temperature (°C.) | Reaction time (hrs.) | Optical rotation $[\alpha]_D^{25}$ (neat) | Yield (%) |
| --- | --- | --- | --- |
| 10 | 6 | −0.2° | 95 |
| 30 | 4 | −0.1° | 90 |
| 50 | 3 | −0.1° | 84 |

EXAMPLE 3

As in Example 1, racemization was carried out at 20° C. The optical rotation and the yield of the product with variation of the amount of the catalyst and the reaction time were as shown in Table 3.

TABLE 3

| Sodium naphthalene (sodium: naphthalene = 1:1 by mole) (g) | Reaction time (hrs.) | Optical rotation $[\alpha]_D^{25}$ (neat) | Yield (%) |
| --- | --- | --- | --- |
| 1.5 | 10 | −0.2° | 93 |
| 2.0 | 6 | −0.3° | 93 |
| 2.5 | 4 | −0.4° | 90 |
| 3.0 | 3 | −0.2° | 88 |

EXAMPLE 4

In a 100 ml reactor, there was charged (−)-β-phenyl-α-(p-tolyl)ethylamine ($[\alpha]_D^{25}$ −8.9° (neat)) (50 g under nitrogen. After sodium naphthalene (sodium:naphthalene=1:1 by mole) (2.0 g) was added thereto, the resultant mixture was stirred at 25° C. for 7 hours. The reaction mixture was treated as in Example 1 to give racemic β-phenyl-α-(p-tolyl)ethylamine (45.3 g) as a fraction boiling at 108° to 109° C./0.07 mmHg. $[\alpha]_D^{25}$ −0.2° (neat). $n_D^{25}$ 1.5718.

EXAMPLE 5

In a 100 ml reactor, there was charged (+)-α,β-diphenylethylamine ($[\alpha]_D^{25}$ +13.4° (neat)) (50 g) under nitrogen. After sodium naphthalene (sodium:naphthalene=1:1 by mole) (2.0 g) was added thereto, the resultant mixture was stirred at 25° C. for 6 hours. The reaction mixture was treated as in Example 1 to give racemic α,β-diphenylethylamine (46.2 g) as a fraction boiling at 114° to 116° C./0.3 mmHg. $[\alpha]_D^{25}$ +0.1° (neat).

EXAMPLE 6

In a 100 ml reactor, there was charged (−)-α- phenyl-β-(p-tolyl)ethylamine ($[\alpha]_D^{25}$ −8.9° (neat)) (50 g) under nitrogen. After sodium anthracene (sodium:anthracene=11.4:88.6 by weight, i.e. 1:1 by mole) (3.0 g) was added thereto, the resultant mixture was stirred at 20° C. for 5 hours. The reaction mixture was treated as in Example 1 to give racemic α-phenyl-β-(p-tolyl)-ethylamine (42.6 g) as a fraction boiling at 120° to 123° C./0.2 mmHg. $[\alpha]_D^{25}$ −0.1° (neat).

EXAMPLE 7

In a 300 ml reactor, there was charged anhydrous tetrahydrofuran (50 g) under nitrogen. After the addition of naphthalene (5.1 g) and metallic sodium (0.9 g), the resultant mixture was stirred at room temperature whereby the metallic sodium was dissolved to produce a dark green colored complex. Stirring was continued for 2 hours, (−)-β-phenyl-α-(p-tolyl)ethylamine ($[\alpha]_D^{25}$ −8.6° (neat)) (100 g) was added thereto, and then stirring was further continued at room temperature for 7 hours, whereby racemization was completed. The optical rotation of the resulting product was confirmed to be 0°.

EXAMPLE 8

In a 100 ml reactor, there was charged (−)-α-(1-naphthyl)ethylamine ($[\alpha]_D^{20}$ −81.3° (neat)) (50 g) under nitrogen. After sodium naphthalene (sodium:naphthalene=1:1 by mole) (2.0 g) was added thereto, the resultant mixture was stirred at 25° C. The optical rotation of the reaction mixture measured with elapse of the reaction time was as shown in Table 4.

TABLE 4

| Reaction time (hrs.) | Optical rotation $[\alpha]_D^{25}$ (c 1, ethanol) |
| --- | --- |
| 0 | −57.0° |
| 3 | −25.3° |
| 7 | −5.9° |
| 9 | −1.4° |

After completion of the reaction, the reaction mixture was treated as in Example 1 to give racemic α-(1-napthyl)ethylamine (45.0 g) as a fraction boiling at 123° to 126° C./2.0 mmHg. $n_D^{25}$ 1.6216.

EXAMPLE 9

As in Example 8, (−)-α-phenylethylamine ($[\alpha]_D^{20}$ −39° (neat)) (50 g) was treated with sodium naphthalene (sodium:naphthalene=1:1 by mole) (3.0 g) at 25° C. for 6 hours. The reaction mixture was treated as in Example 1 to give racemic α-phenylethylamine (42.6 g) as a fraction boiling at 105° to 107° C./53 mmHg. $[\alpha]_D^{20}$ −0.1° (neat). $n_D^{20}$ 1.5252.

EXAMPLE 10

As in Example 8, (+)-α-(1-naphthyl)ethylamine ($[\alpha]_D^{20}$ +81.3° (neat)) (50 g) was treated with sodium anthracene (sodium:anthracene=1:1 by mole) (3.0 g) at 20° C. for 9 hours. The reaction mixture was treated as in Example 1 to give racemic α-(1-naphthyl)ethylamine (45.3 g) as a fraction boiling at 124 to 126° C./2.0 mmHg. $[\alpha]_D^{20}$ +0.1° (neat).

EXAMPLE 11

In a 300 ml reactor, there was charged anhydrous tetrahydrofuran (50 g) under nitrogen. After the addition of naphthalene (5.1 g) and metallic sodium (0.9 g), the metallic sodium was dissolved to produce a dark green colored complex. Stirring was continued for 2 hours, (−)-α-phenylethylamine ($[\alpha]_D^{20}$ −39° (neat)) (100 g) was added thereto, and then stirring was further continued at room temperature for 9 hours, whereby racemization was completed. The optical rotation of the resulting product was confirmed to be 0°.

EXAMPLE 12

In a 100 ml reactor, there was charged L-β-phenylalanine methyl ester ($[\alpha]_D^{25}$ +22.3° (neat)) (50 g) under nitrogen. After sodium naphthalene (sodium:naphthalene=1:1 by mole) (1.3 g) was added thereto, the resultant mixture was stirred at 23° C. The optical rotation of the reaction mixture measured with elapse of the reaction time was as shown in Table 5.

TABLE 5

| Reaction time (min.) | Optical rotation $[\alpha]_D^{23}$ (c 1, ethanol) |
| --- | --- |
| 0 | +27.9° |
| 10 | +17.0° |
| 30 | +12.4° |
| 60 | +5.8° |
| 120 | +3.0° |
| 180 | +1.1° |

After completion of the reaction, the catalyst was eliminated from the reaction mixture, and distillation was carried out to give racemic β-phenylalanine methyl ester (45.3 g) as a fraction boiling at 88° to 92° C./0.3 mmHg. $[\alpha]_D^{23}$ +0.8° (neat).

EXAMPLE 13

In a 100 ml flask, there was charged L-alanine ethyl ester ($[\alpha]_D^{22}$ −2.2° (neat)) (50 g) under nitrogen. After potassium naphthalene (potassium:naphthalene=1:1 by mole) (1.6 g) was added thereto, the resultant mixture was stirred at 22° C. for 3 hours. The catalyst was eliminated from the reaction mixture, and distillation was carried out to give racemic alanine ethyl ester (46.2 g) as a fraction boiling at 55° to 56° C./22 mmHg. The optical rotation of the product was confirmed to be 0°.

EXAMPLE 14

In a 25 ml reactor, there was charged L-leucine ethyl ester ($[\alpha]_D^{20}$ +13.1° (neat)) (10 g) under nitrogen. After sodium naphthalene (sodium:naphthalene=1:1 by mole) (0.8 g) was added thereto, the resultant mixture was stirred at 15° C. for 4 hours. The catalyst was eliminated from the reaction mixture, and distillation was carried out to give racemic leucine ethyl ester (9.1 g) as a fraction boiling at 83° to 84° C./12 mmHg. $[\alpha]_D^{20}$ +0.1° (neat).

EXAMPLE 15

In a 25 ml reactor, there was charged diethyl L-aspartate ($[\alpha]_D^{25}$ −9.5° (neat)) (10 g) under nitrogen. After sodium anthracene (sodium:anthracene=1:1 by mole) (0.8 g) was added thereto, the resultant mixture was stirred at 25° C. The optical rotation of the reaction mixture measured with elapse of the reaction time was as shown in Table 6.

TABLE 6

| Reaction time (min.) | Optical rotation $[\alpha]_{365}^{25}$ (c 1, chloroform) |
| --- | --- |
| 0 | −21.5° |
| 10 | −16.5° |
| 20 | −10.7° |
| 30 | −4.6° |
| 60 | −2.2° |
| 120 | −0.9° |

After completion of the reaction, the catalyst was eliminated from the reaction mixture, and distillation was carried out to give racemic diethyl aspartate (8.7 g) as a fraction boiling at 85° to 86° C./1.0 mmHg. $[\alpha]_D^{25}$ −0.3° (neat).

What is claimed is:

1. A method for the racemization of optically active amines which comprises contacting an optically active amine of the formula:

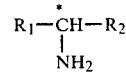

$$R_1-\overset{*}{\underset{NH_2}{C}H}-R_2$$

wherein C* is an asymmetric carbon atom, $R_2$ is alkyl, aralkyl or aryl and $R_2$ is alkoxycarbonyl, the aryl or aralkyl moiety being unsubstituted or being substituted with one or more alkyl or alkoxy groups on the aromatic ring, with about 1/1000 to 1/5 mole per 1 mole of the optically active amine of an alkali metal polycyclic aromatic hydrocarbon catalyst at a temperature of from about −10° to 150° C.

2. The method according to claim 1, wherein $R_2$ is an alkoxycarbonyl group having not more than 9 carbon atoms.

3. The method according to claim 1, wherein the alkali metal polycyclic aromatic hydrocarbon catalyst is at least one member selected from the group consisting of sodium naphthalene and potassium naphthalene.

4. The method according to claim 1, wherein the contact is effected at a temperature of from about $-10°$ to $100°$ C.

5. The method according to claim 1, wherein the catalyst is used in an amount of about 1/200 to 1/10 mole per 1 mole of the optically active amine.

6. A method for the racemization of optically active amines which comprises contacting an optically active amine of the formula:

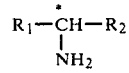

wherein C* is an asymmetric carbon atom, $R_1$ is alkyl of up to 4 carbon atoms, aralkyl of up to 12 carbon atoms, phenyl, naphthyl or phenyl substituted with one methyl group and $R_2$ is alkoxycarbonyl of up to 9 carbon atoms, with about 1/200 to 1/10 mole per 1 mole of an alkali metal polycyclic aromitic hydrocarbon catalyst at a temperature of from about $-10°$ to $100°$ C.

7. The method according to claim 6, wherein the alkali metal polycyclic aromatic hydrocarbon catalyst is at least one member selected from the group consisting of sodium naphthalene and potassium naphthalene.

* * * * *